(12) United States Patent
Hodson et al.

(10) Patent No.: US 7,967,011 B2
(45) Date of Patent: Jun. 28, 2011

(54) INHALATION DEVICE

(75) Inventors: Darren Hodson, Shropshire (GB); Jorgen Rasmussen, Struer (DK)

(73) Assignee: AstraZeneca AB, Sodertalje (SE)

( * ) Notice: Subject to any disclaimer, the term of this patent is extended or adjusted under 35 U.S.C. 154(b) by 1004 days.

(21) Appl. No.: 11/346,558

(22) Filed: Feb. 3, 2006

(65) Prior Publication Data

US 2006/0213510 A1 Sep. 28, 2006

Related U.S. Application Data

(63) Continuation-in-part of application No. 10/698,950, filed on Nov. 3, 2003, now Pat. No. 7,367,333, which is a continuation of application No. 09/986,941, filed on Nov. 13, 2001, now abandoned, which is a continuation of application No. 09/214,757, filed as application No. PCT/SE98/02038 on Nov. 11, 1998, now abandoned.

(30) Foreign Application Priority Data

Nov. 14, 1997 (SE) ...................................... 9704185

(51) Int. Cl.
*A61M 11/00* (2006.01)
*A61M 16/00* (2006.01)
*B05D 7/11* (2006.01)
*B65D 83/06* (2006.01)

(52) U.S. Cl. .......... 128/200.23; 128/200.14; 128/203.15

(58) Field of Classification Search ............. 128/200.14, 128/200.16, 200.21, 200.23, 200.24, 200.12, 128/203.12, 203.14, 203.15, 203.19, 203.21–203.23; 222/153.01–153.04, 153.1–153.14, 182
See application file for complete search history.

(56) References Cited

U.S. PATENT DOCUMENTS

| | | | | |
|---|---|---|---|---|
| 784,513 A * | 3/1905 | Brockelbank | ................. | 215/332 |
| 2,396,866 A * | 3/1946 | Lytton | ........................... | 401/244 |
| 2,705,007 A * | 3/1955 | Gerber | ..................... | 128/203.21 |
| 2,865,525 A * | 12/1958 | Satz | .............................. | 215/272 |
| 3,398,848 A * | 8/1968 | Donovan | ...................... | 215/224 |
| 3,456,644 A | 7/1969 | Theil | ......................... | 128/200.23 |
| 3,506,004 A | 4/1970 | Mann et al. | ............. | 128/200.23 |
| 3,521,643 A | 7/1970 | Toth | ......................... | 128/202.21 |
| 3,636,949 A | 1/1972 | Kropp | ....................... | 128/200.23 |
| 3,703,975 A * | 11/1972 | Wittemer | ..................... | 215/213 |
| 3,720,342 A * | 3/1973 | Vercillo | ....................... | 215/224 |
| 3,739,950 A | 6/1973 | Gorman | | |
| 3,789,843 A | 2/1974 | Armstrong et al. | ...... | 128/200.23 |
| 3,818,908 A | 6/1974 | Phillips | ..................... | 128/200.14 |
| 3,863,798 A * | 2/1975 | Kurihara et al. | ............ | 215/301 |
| 3,870,182 A * | 3/1975 | Georgi | .......................... | 215/220 |
| 3,927,783 A * | 12/1975 | Bogert | ......................... | 215/222 |

(Continued)

FOREIGN PATENT DOCUMENTS

WO 95/07723 3/1995

(Continued)

*Primary Examiner* — Kristen C Matter
(74) *Attorney, Agent, or Firm* — Finnegan, Henderson, Farabow, Garrett, & Dunner, LLP

(57) ABSTRACT

Actuator for an inhaler for delivering medicament by inhalation, having a mouthpiece for guiding medicament to the mouth of a user; and a removable protection cap for the mouthpiece. The cap is secured to the mouthpiece by a cap retaining member that engages a mating recess in the mouthpiece outer periphery. The cap includes at least one release button arranged to provide an elastic deformation of the cap inner periphery that disengages the cap retaining member from the recess.

20 Claims, 5 Drawing Sheets

U.S. PATENT DOCUMENTS

| | | | | |
|---|---|---|---|---|
| 4,171,057 A | * | 10/1979 | Gach | 215/211 |
| 4,335,823 A | * | 6/1982 | Montgomery et al. | 215/206 |
| 4,480,762 A | * | 11/1984 | Thomas | 215/273 |
| 4,534,343 A | | 8/1985 | Nowacki et al. | 128/200.23 |
| 4,576,157 A | * | 3/1986 | Raghuprasad | 128/200.23 |
| 4,641,644 A | | 2/1987 | Andersson et al. | |
| 4,694,824 A | * | 9/1987 | Ruderian | 128/203.22 |
| 4,796,614 A | | 1/1989 | Nowacki et al. | 128/200.14 |
| 4,834,083 A | | 5/1989 | Byram et al. | 128/200.23 |
| 4,944,429 A | * | 7/1990 | Bishop et al. | 222/153.13 |
| 5,027,808 A | | 7/1991 | Rich et al. | 128/203.23 |
| 5,033,463 A | * | 7/1991 | Cocozza | 128/203.21 |
| 5,060,643 A | | 10/1991 | Rich et al. | 128/200.23 |
| 5,184,761 A | | 2/1993 | Lee | 222/402.2 |
| 5,217,004 A | | 6/1993 | Blasnik et al. | 128/200.23 |
| 5,520,166 A | | 5/1996 | Ritson et al. | |
| 5,687,863 A | * | 11/1997 | Kusz | 215/216 |
| 5,758,638 A | * | 6/1998 | Kreamer | 128/200.23 |
| 5,823,394 A | | 10/1998 | Davis et al. | 222/137 |
| 6,055,979 A | * | 5/2000 | Fuchs | 128/203.15 |
| 6,062,214 A | | 5/2000 | Howlett | |
| 6,277,749 B1 | | 8/2001 | Funabashi | |
| 6,345,617 B1 | * | 2/2002 | Engelbreth et al. | 128/200.23 |
| 6,427,684 B2 | | 8/2002 | Ritsche et al. | 128/200.23 |
| 6,439,409 B1 | * | 8/2002 | Dressel et al. | 215/228 |
| 6,446,626 B1 | * | 9/2002 | Virtanen | 128/200.14 |
| 6,453,190 B1 | | 9/2002 | Acker et al. | |
| 6,494,201 B1 | | 12/2002 | Welik | 128/200.23 |

FOREIGN PATENT DOCUMENTS

| | | |
|---|---|---|
| WO | 96/04948 | 2/1996 |
| WO | 96/04949 | 2/1996 |

* cited by examiner

INHALATION DEVICE

This application is a continuation-in-part of application Ser. No. 10/698,950, filed Nov. 3, 2003, U.S. Pat. No. 7,367,333, which is a continuation of application Ser. No. 09/986,941, filed Nov. 13, 2001, abandoned, which is a continuation of Ser. No. 09/214,757, filed Jan. 12, 1999, which is a 371 of PCT/SE98/02038, filed Nov. 11, 1998, abandoned, the entire content of which is hereby incorporated by reference in this application.

The present invention relates to an actuator for an inhaler for administering medicament by inhalation and to an inhaler including the same.

BACKGROUND OF THE INVENTION

For some time, actuators have been known for delivering metered doses of medicament from aerosol canisters. Conventionally, these actuators comprise a tubular member for receiving a canister containing medicament; a mouthpiece for guiding medicament to the mouth of a user. In order to prevent dust etc. from entering the mouth piece when the actuator is not used, the actuator further may comprise a removable protection cap for the mouthpiece. The actuator, except for the protection cap, can be comprised of a single integral moulding in plastic material, or an assembly of two or more parts. It is of great importance that the protection cap is reliably attached to the mouth piece, to prevent dust or foreign particles etc. being collected within the inhaler and contaminating the inhaler at worst being inhaled or blocking the delivery channel. Therefore it is important to maintain cleanliness of the inhaler. However, it is of equal importance that the protection cap is simple to remove, so that any patient, for example, a physically impaired patient, is able to remove it and use the inhaler without hindrance.

SUMMARY OF THE INVENTION

It is an aim of the present invention to provide an actuator, with an improved protection cap for the mouth piece.

Accordingly, the present invention provides an actuator for an inhaler for delivering medicament by inhalation, comprising a mouthpiece for guiding medicament to the mouth of a user; and a removable protection cap for the mouthpiece, wherein the cap is secured to the mouthpiece by a cap retaining member that engages a mating recess in the mouthpiece outer periphery, and wherein the cap comprises at least one release button arranged to provide an elastic deformation of the cap inner periphery that disengage the cap retaining member from the recess.

According to one embodiment, the section of the cap inner periphery comprising the retaining member encloses the outer periphery of the mouthpiece in a close mating relationship, and the release button is comprised of a transverse section of the cap inner periphery that is spaced apart from the mouthpiece outer periphery.

Preferably, the cap comprises at least two buttons, and in the disclosed embodiment, the cap comprises two diametrically arranged release buttons. In order for the cap to be easy to remove it is suitable to provide it with two diametrically arranged release buttons as is disclosed in FIGS. 1 to 6.

According to one embodiment, the mouthpiece is comprised of an ovoid tubular section, wherein the retaining member is arranged about the minor axis, and the release buttons are arranged about the major axis. Preferably, the cap comprises an essentially ovoid mating section with bulged sections about the major axis forming the release buttons.

The present invention also extends to an inhaler comprising the above-described actuator and a canister containing medicament.

Preferably, the inhaler is a pressurised metered dose inhaler.

BRIEF DESCRIPTION OF THE DRAWINGS

A preferred embodiment of the present invention will now be described herein below by way of example only with reference to the accompanying drawings, in which.

DETAILED DESCRIPTION OF PREFERRED EMBODIMENTS

Figure 1:
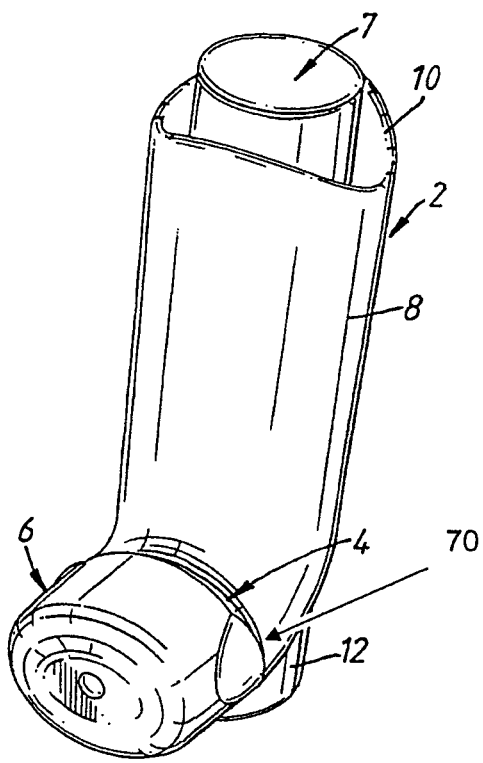
FIG. 1 illustrates a perspective view of an inhaler in accordance with a preferred embodiment of the present invention.
Figure 2:
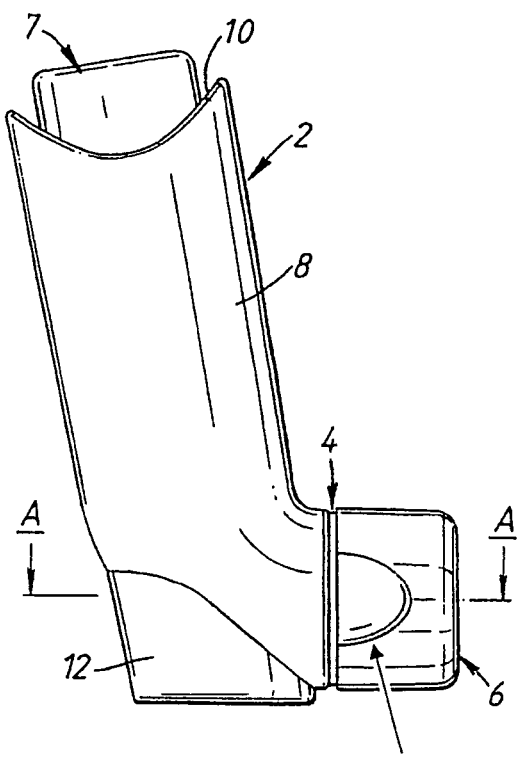
FIG. 2 illustrates a side view of the inhaler of FIG. 1.
Figure 3:
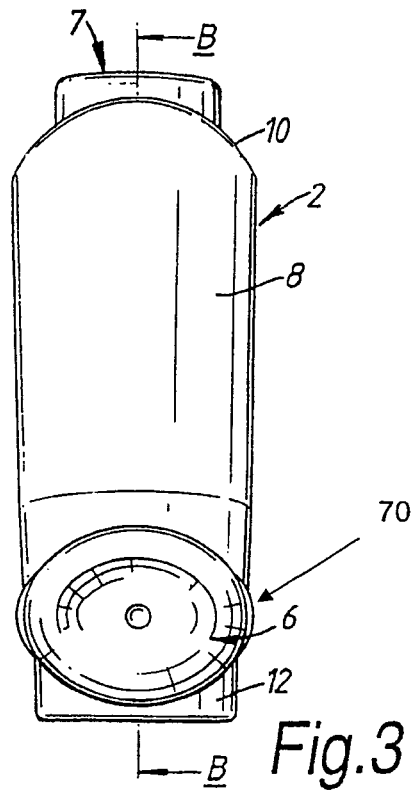
FIG. 3 illustrates a front view of the inhaler of FIG. 1.
Figure 4:
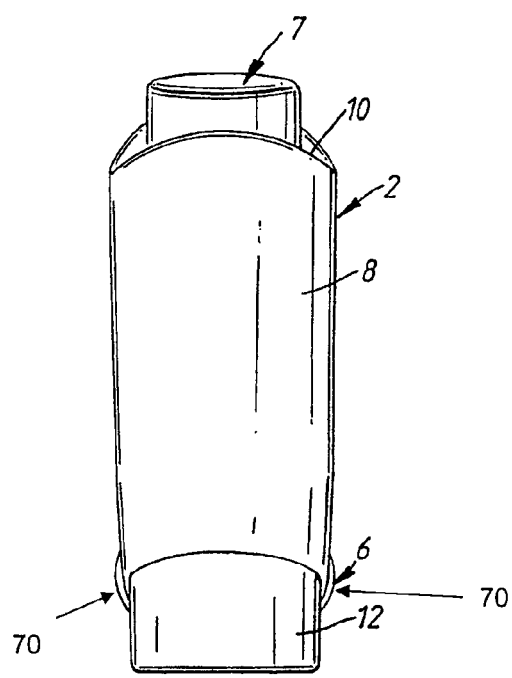
FIG. 4 illustrates a rear view of the inhaler of FIG. 1.
Figure 5:
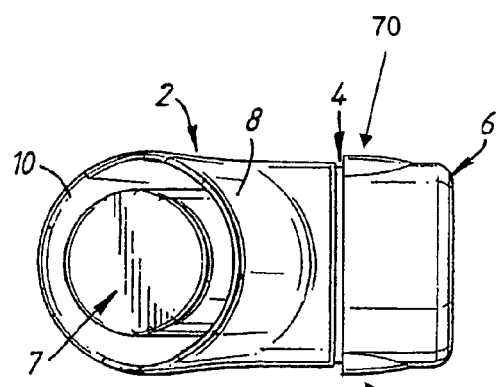
FIG. 5 illustrates a plan view of the inhaler of FIG. 1.
Figure 6:
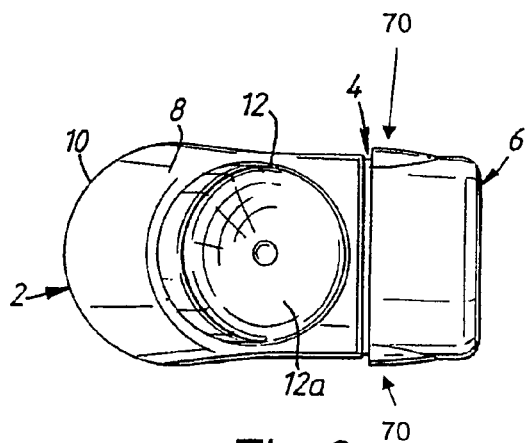
FIG. 6 illustrates an underneath plan view of the inhaler of FIG. 1.

The inhaler comprises an actuator, which comprises a main body 2, an outlet assembly 4 fitted to a lower part of the main body 2 and a cap 6, and an aerosol canister 7 containing medicament fitted therein.

The main body 2 comprises a tubular member 8 having an opening 10 at one, the upper end thereof into which a canister 7 having a valve stem 11 extending therefrom is in use fitted, and a foot 12 having a bottom surface which includes a recess 12a, in this embodiment concave in shape, for receiving typically a thumb of a user. In an alternative embodiment the foot 12 can be formed with a substantially flat bottom surface. The foot 12 serves to allow the actuator to stand unsupported on a flat surface such that, when the actuator is not in use, it can be stored in an upright position. This is particularly advantageous when a canister 7 is fitted therein, since such canisters 7 should, ideally, be stored with the valve stem 11 directed downwards. The other, lower, end of the tubular member 8 is closed and includes a lateral opening 14, in this embodiment ovoid in shape, into which the outlet assembly 4 is fitted.

The main body 2 further comprises a pair of opposing projections 16 which extend inwardly from the inner surface of the tubular member 8 adjacent the lateral opening 14. The projections 16 are disposed to the sides of the lateral opening 14 and are spaced rearwardly therefrom.

The outlet assembly 4 comprises a tubular section 18, a major part of which defines the mouthpiece which is in use gripped by the lips of a user, and a nozzle block 20 connected thereto.

Even though the embodiment of the present invention is disclosed herein is an actuator of two part type, as disclosed in great detail below, it is inherently clear that the protection cap does not depend on the type of actuator as long it comprises a mouthpiece. Moreover, the disclosed actuator is a "pressurised metered dose inhaler", but the protection cap can be used to protect the mouthpiece of other types of inhalers.

Figure 10:
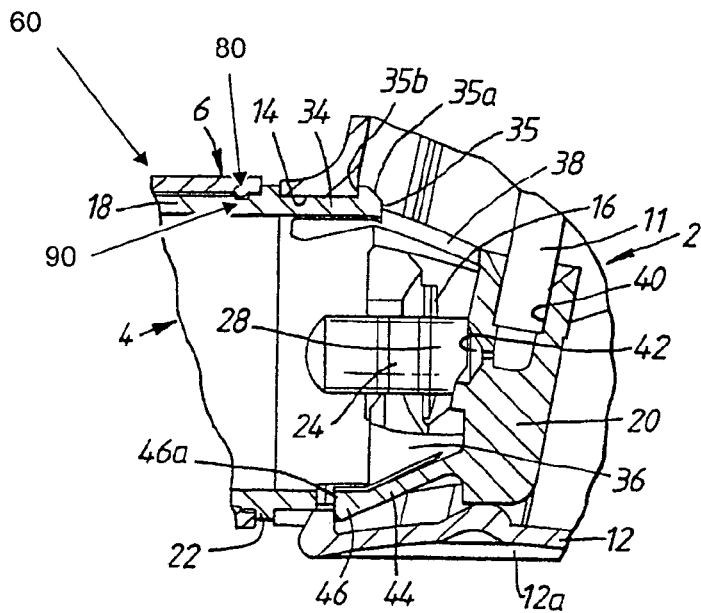
FIG. 10 illustrates in enlarged scale a fragmentary view of the section illustrated in FIG. 9.
Figure 11:
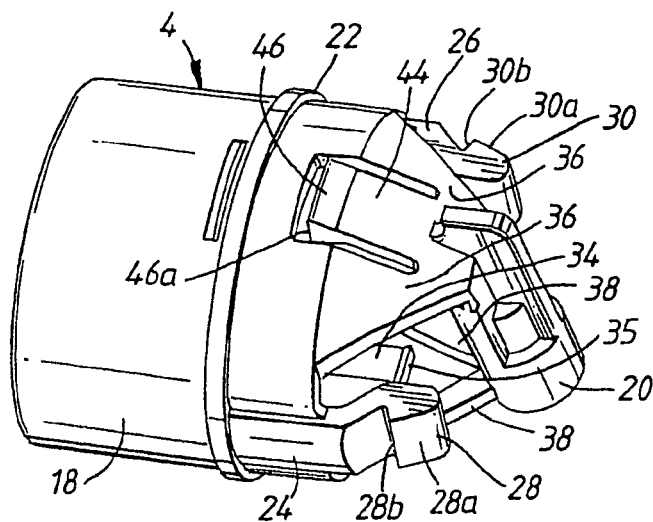
FIG. 11 illustrates a perspective view of the outlet assembly of the actuator of the inhaler of FIG. 1.
Figure 12:
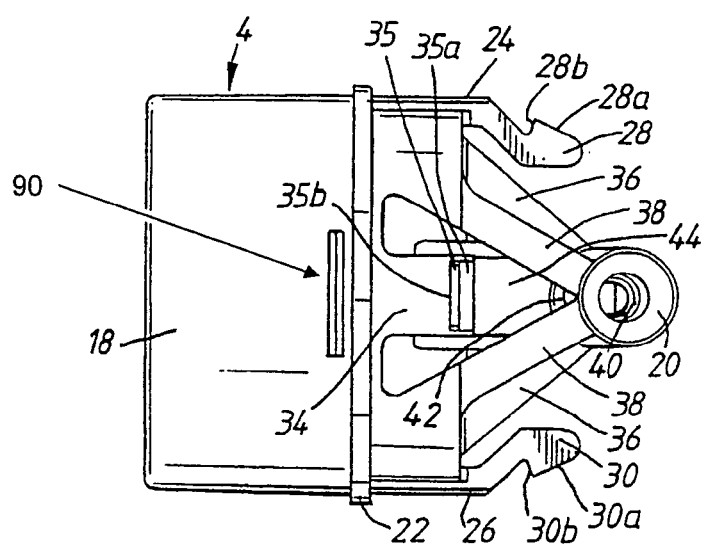
FIG. 12 illustrates a plan view of the outlet assembly of FIG. 11.
Figure 13:
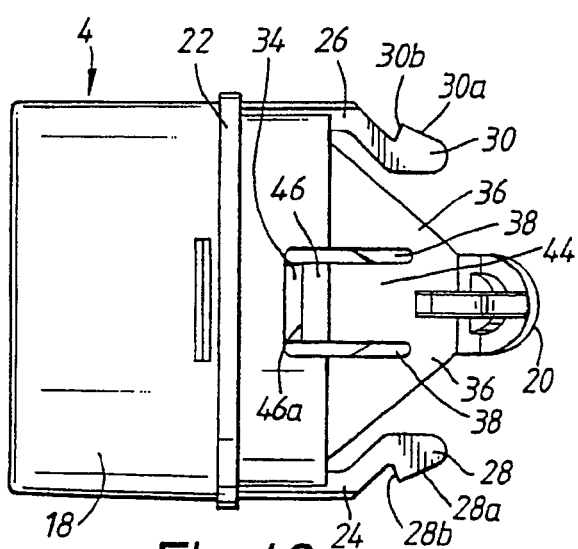
FIG. 13 illustrates an underneath plan view of the outlet assembly of FIG. 11.
Figure 14:
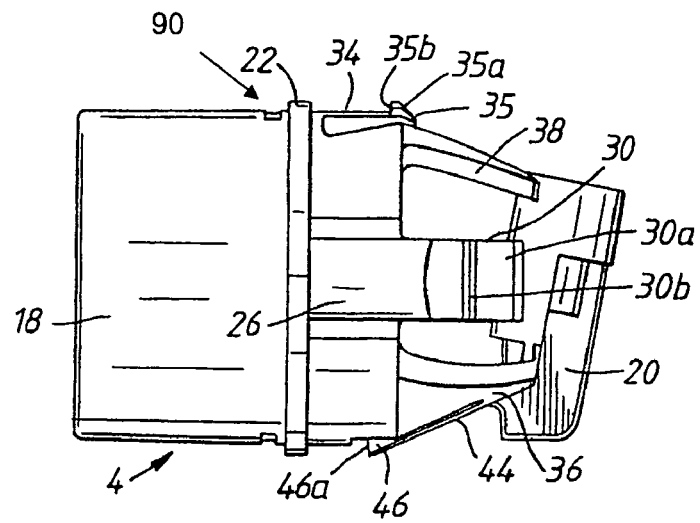
FIG. 14 illustrates a side view of the outlet assembly of FIG. 11.
Figure 15:
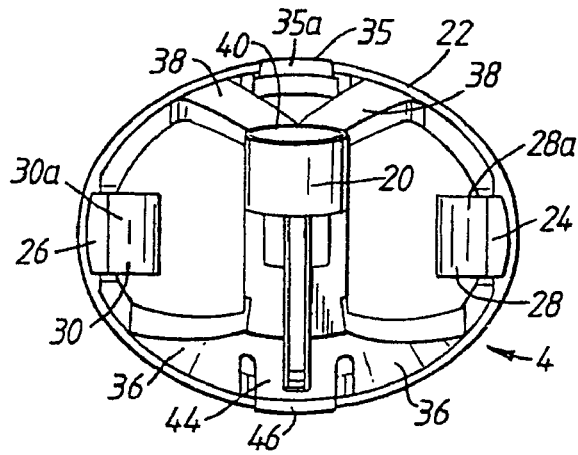
FIG. 15 illustrates a rear view of the outlet assembly of FIG. 11.
Figure 16:
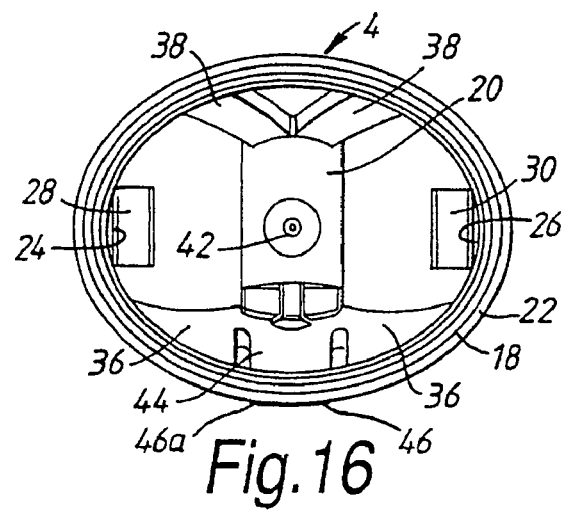
FIG. 16 illustrates a front view of the outlet assembly of FIG. 11.

The actuator according to the present invention is clearly disclosed in the figures. From FIGS. 1 to 6 and especially in FIGS. 7 to 10 it can be seen that the protection cap 6 comprises a cap section 60 that closely mates the outer surface of the mouthpiece, and two diametrically arranged release buttons 70. In FIG. 10, reference number 80 is a retaining member that extends along the mouthpiece diameter and engages a mating recess 90 in the mouthpiece outer periphery thereby securing the cap to the mouthpiece.

Figure 7:
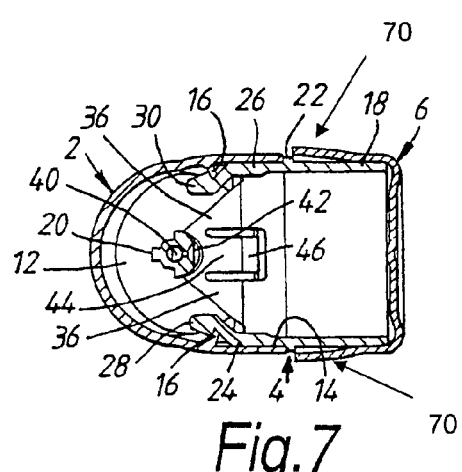
FIG. 7 illustrates a horizontal sectional view (along section A-A) of the inhaler of FIG. 1.
Figure 8:
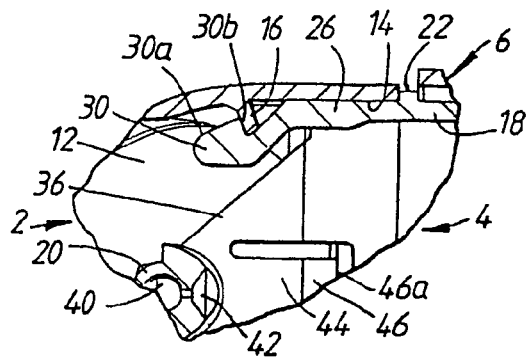
FIG. 8 illustrates in enlarged scale a fragmentary view of the section illustrated in FIG. 7.
Figure 9:
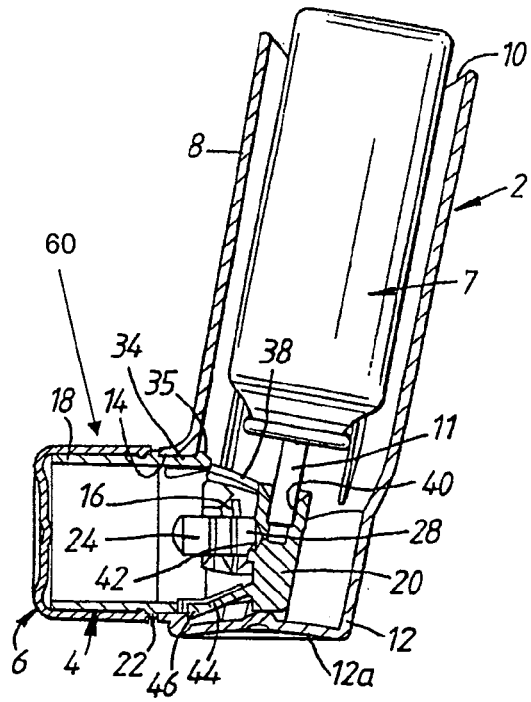
FIG. 9 illustrates a vertical sectional view (along section B-B) of the inhaler of FIG. 1.

More in detail, it can be seen in FIG. 7 that the release buttons 70 are formed as sections of the cap inner periphery that is spaced apart from the mouthpiece 18 outer periphery. Due to the design of the release buttons 70 on the protection cap 6, the buttons 70, when pushed, will provide an elastic deformation of the cap inner periphery that disengage the cap retaining member 80 from the recess 90.

In the disclosed embodiment the cap comprises two buttons, but it could alternatively comprise one single button or three or more buttons. According to one embodiment, a cap comprising three or more buttons is designed as a child safety cap, only being possible to remove e.g. when applying equal pressure on all buttons simultaneously, or when applying pressure on the buttons in a predetermined sequence etc. and in the disclosed embodiment, the cap comprises two diametrically arranged release buttons. In order for the cap to be easy to remove it is suitable to provide it with two diametrically arranged release buttons as is disclosed in FIGS. 1 to 6.

According to the disclosed embodiment, the mouthpiece is comprised of an ovoid tubular section 18, wherein the retaining member 80 is arranged to extend along the minor axis where the cap comprises an essentially ovoid mating section, and the release buttons 70 are arranged as bulged sections diametrically about the major axis. When the cap 6 is placed on the mouthpiece the retaining member 80 will engage the recess 90, and the bulged sections forming the release buttons 70 being spaced apart from the mouthpiece. When the release buttons 70 are pressed, the bulged sections are forced towards the mouthpiece whereby the mating section of the cap comprising the retaining member 80 is lifted from the mouthpiece and disengages the recess 90. Thereafter the cap can be removed by preserving the release pressure and removing the cap 6 from the mouthpiece.

The tubular section 18 includes a radial outwardly-directed peripheral flange 22. When the outlet assembly 4 is inserted fully into the main body 2, the flange 22 abuts the lateral opening 14 such that the major part of the tubular section 18 extends outwardly of the main body 2.

The outlet assembly 4 further comprises first and second arms 24, 26 which extend rearwardly form respective sides of the tubular section 18. Each of the first and second arms 24, 26 includes a catch member 28, 30 which is adapted to engage with a respective one of the projections 16 on the inner surface of the tubular member 8 when the outlet assembly 4 is inserted fully into the main body 2. The catch members 28, 30 on the first and second arms 24, 26 each include a first surface 28a, 30a which has a rearwardly directed component and acts as a guiding surface, and a second surface 28b, 30b which is substantially orthogonally directed to the longitudinal axis of the outlet assembly 4 and acts as a locking surface.

The outlet assembly 4 further comprises a third arm 34 which extends rearwardly from the top of the tubular section 18. The third arm 34 includes a catch member 35 in the form of an outwardly-directed projection, which, when the outlet assembly 4 is inserted fully into the main body 2, engages behind a part of the tubular member 8 defining the lateral opening 14. The catch member 35 on the third arm 34, as with the catch members 28, 30 on the first and second arms 24, 26, includes a first surface 35a which has a rearwardly directed component and acts as a guiding surface, and a second surface 35b which is substantially orthogonally directed to the longitudinal axis of the outlet assembly 4 and acts as a locking surface.

The nozzle block 20 is connected to the tubular section 18 by first and second pairs of connecting elements 36, 38. The first pair of connecting elements 36 extend between a lower part of the nozzle block 20 and a lower part of the tubular section 18. As will be described herein below, in this embodiment the lower connecting elements 36 are configured to break or be permanently deformed on withdrawal of the outlet assembly 4 from the main body 2. The second pair of connecting elements 38 extend between an upper part of the nozzle block 20 and an upper part of the tubular section 18. The nozzle block 20 includes a tubular bore 40 which extends along the longitudinal axis of the tubular member 8 when the outlet assembly 4 is inserted fully into the main body 2. The tubular bore 40 is open at one, the upper, end and includes a laterally-directed spray orifice 42 at the other, lower, end. The spray orifice 42 is configured to direct a spray into the tubular section 18. In this embodiment the tubular bore 40 is adapted to receive the valve stem 11 of a canister 7.

The outlet assembly 4 further comprises a fourth arm 44 which extends forwardly and downwardly from the nozzle block 20. The distal end of the fourth arm 44 includes a catch member 46 which, when the outlet assembly 4 is inserted fully into the main body 2, engages behind a part of the tubular member 8 defining the lateral opening 14. The catch member 46 on the fourth arm 44 includes a surface 46a which is substantially orthogonally directed to the longitudinal axis of the outlet assembly 4 and acts as a locking surface.

In manufacture, an outlet assembly 4 and a main body 2 are selected according to the requirements, based on colour, shape, etc., for the actuator. The outlet assembly 4 is then inserted into the lateral opening 14 in the main body 2 until the catch members 28, 30 on the first and second arms 24, 26 of the outlet assembly 4 engage with the respective projections 16 on the inner side surface of the tubular member 8 of the main body 2, and the catch members 34, 46 on the third and fourth arms 34, 44 of the outlet assembly 4 engage behind respective parts of the tubular member 8 defining the lateral opening 14. A canister 7 is then passed into the tubular member 8 of the main body 2 through the upper opening 10 such that the valve stem 11 of the canister 7 is located in the tubular bore 40 in the nozzle block 20. The inhaler is then ready for use.

By the provision of catch members the outlet assembly 4 is held in the main body 2 and the outlet assembly 4 cannot be non-destruct ably detached from the main body 2. As mentioned herein above, the outlet assembly 4 is configured to break or be permanently deformed if withdrawn from the main body 2 and thereby render the outlet assembly 4 and hence the actuator unusable. In this embodiment this is achieved by configuring the lower connecting elements 36 connecting the tubular section 18 and the nozzle block 20 of the outlet assembly 4 to break or be permanently deformed on withdrawal of the outlet assembly 4 from the main body 2.

Finally, it will be understood by a person skilled in the art that the present invention is not limited to the described embodiment but can be modified in many different ways within the scope of the appended claims.

The invention claimed is:

1. An actuator for an inhaler for delivering medicament by inhalation, the actuator comprising:
    a main body tubular member having a longitudinal opening configured to receive a medicament canister, and a lateral ovoid opening configured to receive a mouthpiece;
    an ovoid, tubular mouthpiece having a major axis, a minor axis, an outer periphery, a mating recess formed in the outer periphery at an end of the minor axis, and at least one catch arm for engaging the lateral ovoid opening in the main body tubular member; and
    a removable protection cap for the mouthpiece, said cap having a cap major axis, a cap minor axis, a cap retaining member disposed in a cap inner periphery and extending along the cap minor axis for engaging the mating recess formed in the mouthpiece, and a release button formed in the cap at each end of the cap major axis;
    wherein the release buttons on either end of the cap major axis are arranged to provide an elastic deformation of the cap inner periphery, which disengages the cap retaining member from the mating recess without disengaging the at least one catch arm from the lateral ovoid opening in the main body tubular member.

2. The actuator according to claim 1, wherein a section of a cap inner periphery comprising the cap retaining member encloses the mouthpiece outer periphery in a close mating relationship, and the release buttons each include a transverse section of cap inner periphery that is spaced apart from the mouthpiece outer periphery.

3. The actuator according to claim 1, wherein the mouthpiece includes first and second catch arms disposed at opposing ends of the major axis of the mouthpiece, for engaging the lateral ovoid opening in the main body tubular member.

4. The actuator according to claim 1, wherein the mouthpiece includes first and second catch arms disposed at opposing ends of the minor axis of the mouthpiece, for engaging the lateral ovoid opening in the main body tubular member.

5. The actuator according to claim 1, wherein the mouthpiece includes first and second catch arms disposed at opposing ends of the minor axis of the mouthpiece, and third and fourth catch arms disposed at opposing ends of the major axis of the mouthpiece, for engaging the lateral ovoid opening in the main body tubular member.

6. The actuator according to claim 1, wherein the cap comprises an essentially ovoid mating section, with bulged sections about the major axis forming the release buttons.

7. An inhaler comprising the actuator according to claim 1 and a canister containing medicament disposed in the longitudinal opening of the main body tubular member.

8. The inhaler according to claim 7, wherein the inhaler is a pressurized metered dose inhaler.

9. An inhaler for delivering medicament by inhalation, the inhaler comprising:
    an actuator comprising:
        a main body tubular member having a longitudinal opening configured to receive a medicament canister, and a lateral ovoid opening configured to receive a mouthpiece;
        an ovoid, tubular mouthpiece having a major axis, a minor axis, an outer periphery, a mating recess formed in said mouthpiece outer periphery at an end of the minor axis, and at least one catch arm for engaging the lateral ovoid opening in the main body tubular member; and
        a removable protection cap for the mouthpiece, said cap having a cap major axis, a cap minor axis, a cap retaining member disposed in a cap inner periphery and extending along the cap minor axis for engaging the mating recess formed in the mouthpiece, and a release button formed in the cap at each end of the cap major axis; and
    a canister containing medicament disposed in the longitudinal opening of the main body tubular member of the actuator;
    wherein the release buttons on either end of the cap major axis are arranged to provide an elastic deformation of the cap inner periphery, which disengages the cap retaining member from the mating recess without disengaging the at least one catch arm from the lateral ovoid opening in the main body tubular member.

10. The inhaler according to claim 9, wherein a section of a cap inner periphery comprising the cap retaining member encloses the mouthpiece outer periphery in a close mating relationship, and the release buttons each include a transverse section of cap inner periphery that is spaced apart from the mouthpiece outer periphery.

11. The inhaler according to claim 9, wherein the mouthpiece includes first and second catch arms disposed at opposing ends of the major axis of the mouthpiece, for engaging the lateral ovoid opening in the main body tubular member.

12. The inhaler according to claim 9, wherein the mouthpiece includes first and second catch arms disposed at opposing ends of the minor axis of the mouthpiece, for engaging the lateral ovoid opening in the main body tubular member.

13. The inhaler according to claim 9, wherein the mouthpiece includes first and second catch arms disposed at opposing ends of the minor axis of the mouthpiece, and third and fourth catch arms disposed at opposing ends of the major axis of the mouthpiece, for engaging the lateral ovoid opening in the main body tubular member.

14. The inhaler according to claim 9, wherein the cap comprises an essentially ovoid mating section, with bulged sections about the major axis forming the release buttons.

15. The inhaler according to claim 9, wherein the inhaler is a pressurized metered dose inhaler.

16. An actuator for an inhaler for delivering medicament by inhalation, the actuator comprising:
    a main body tubular member having a longitudinal opening configured to receive a medicament canister, and a lateral opening configured to receive a mouthpiece;
    a tubular mouthpiece having an outer periphery, a mating recess formed in the mouthpiece outer periphery on a top side of the mouthpiece, and at least one catch arm disposed on the mouthpiece for engaging the lateral opening in the main body tubular member; and
    a removable protection cap for the mouthpiece, said cap having a cap retaining member disposed in a cap inner periphery and extending along a diameter of the mouthpiece to engage the mating recess, and at least two release buttons formed in the cap on opposing lateral sides of the mouthpiece;
    wherein the release buttons are arranged to provide an elastic deformation of the cap inner periphery, so as to disengage the cap retaining member from the mating recess without disengaging the at least one catch arm from the lateral opening in the main body tubular member.

17. The actuator according to claim 16, wherein a section of cap inner periphery comprising the cap retaining member encloses the mouthpiece outer periphery in a close mating relationship, and the release buttons each include a transverse section of cap inner periphery that is spaced apart from the mouthpiece outer periphery.

18. The actuator according to claim 16, wherein the mouthpiece includes first and second catch arms disposed at opposing lateral sides of the mouthpiece, respectively, for engaging the lateral opening in the main body tubular member.

19. The actuator according to claim 16, wherein the mouthpiece includes first and second catch arms disposed at opposing top and bottom sides of the mouthpiece, respectively, for engaging the lateral opening in the main body tubular member.

20. The actuator according to claim 16, wherein the mouthpiece includes first and second catch arms disposed at opposing lateral sides of the mouthpiece, a third catch arm disposed at a top side of the mouthpiece, and a fourth catch arm disposed at a bottom side of the mouthpiece, for engaging the lateral opening in the main body tubular member.

* * * * *